United States Patent
Watanabe (10) Patent No.: US 7,882,364 B2
(45) Date of Patent: Feb. 1, 2011

(54) TECHNOLOGY FOR AUTHENTICATING PERSON BY DATA GENERATED BASED ON BIOLOGICAL INFORMATION

(75) Inventor: Keisuke Watanabe, Mizuho (JP)

(73) Assignee: Sanyo Electric Co., Ltd., Osaka (JP)

( * ) Notice: Subject to any disclaimer, the term of this patent is extended or adjusted under 35 U.S.C. 154(b) by 1192 days.

(21) Appl. No.: 11/072,405

(22) Filed: Mar. 7, 2005

(65) Prior Publication Data

US 2005/0204149 A1    Sep. 15, 2005

(30) Foreign Application Priority Data

Mar. 15, 2004   (JP)   ............... 2004-073312
Feb. 8, 2005    (JP)   ............... 2005-031814

(51) Int. Cl.
*G06F 21/00* (2006.01)

(52) U.S. Cl. ................. 713/186; 713/185; 713/182

(58) Field of Classification Search .............. None
See application file for complete search history.

(56) References Cited

U.S. PATENT DOCUMENTS

| | | | | |
|---|---|---|---|---|
| 5,598,474 A * | 1/1997 | Johnson | ............ | 713/186 |
| 6,202,151 B1 * | 3/2001 | Musgrave et al. | ............ | 713/186 |
| 6,910,131 B1 * | 6/2005 | Yamada et al. | ............ | 713/186 |
| 6,980,669 B1 * | 12/2005 | Uchida | ............ | 382/115 |
| 7,047,418 B1 * | 5/2006 | Ferren et al. | ............ | 713/186 |
| 7,340,244 B1 * | 3/2008 | Osborne et al. | ............ | 455/414.1 |
| 2002/0109580 A1 * | 8/2002 | Shreve et al. | ............ | 340/5.61 |

FOREIGN PATENT DOCUMENTS

JP          06-155971       6/1994

* cited by examiner

*Primary Examiner*—Pramila Parthasarathy
(74) *Attorney, Agent, or Firm*—McDermott Will & Emery LLP (57) ABSTRACT

A biological information acquisition unit of a biological information processing apparatus acquires biological information. A cue data acquisition unit requests and acquires cue data from the personal authentication apparatus. A personal data generating unit converts the biological information into personal data, or image data. The personal data generating unit further encrypts the personal data based on the cue data. A personal data output unit displays this encrypted personal data on-screen.

10 Claims, 8 Drawing Sheets

TECHNOLOGY FOR AUTHENTICATING PERSON BY DATA GENERATED BASED ON BIOLOGICAL INFORMATION

BACKGROUND OF THE INVENTION

1. Field of the Invention

The present invention relates to a personal authentication apparatus.

2. Description of the Related Art

Methods for personal authentication are broadly classified into three categories. One is authentication based on possessions such as a key and an ID card (for example, see Japanese Patent Laid-Open Publication No. Hei 6-155971). The possession-based authentication, however, is under security threats ascribable to loss and theft. Another is authentication by knowledge such as a password. Nevertheless, the knowledge-based authentication also has security problems due to oblivion, undertook, etc. The other authentication method which has been attracting attention in recent years is biological authentication using biological information such as fingerprints, palm prints, faces, irises, and voice prints. The biological authentication considerably suppresses the security threats ascribable to "loss" which can occur in the foregoing possession- and knowledge-based authentications. In addition, since the users "need not possess" any object or knowledge, it is easy to provide an authentication system of high convenience.

Because of these advantages, personal authentication apparatuses based on biological information are expected to replace the authentication based on possessions such as a house key and a car key. Recent years have seen the emergence of active e-commerce, which often uses knowledge-based authentication methods. Even in this field, authentication apparatuses of higher convenience and safety have been awaited.

In the personal authentication based on biological information, it is necessary to detect features of personal biological information with high precision. Personal authentication by such biological information as a fingerprint and a palm print are how becoming available with relatively high accuracies of authentication. Nevertheless, the sensors of the authentication apparatuses tend to be unsanitary, being touched by an unspecified number of users. The authentication methods using irises and retinas also have the same problem because the users bring their faces as close to the authentication apparatuses as almost into touch with. On this account, many users have psychological resistance more or less against the personal authentication apparatuses that acquire biological information by contact or such means (hereinafter, referred to collectively as "contact-type personal authentication apparatuses"). In particular, fingerprints have long been used in criminal investigations by the police. This historical background makes users liable to avoid the personal authentication based on fingerprints. As described above, contact-type personal authentication apparatuses are generally poor in acceptability.

On the other hand, personal authentication apparatuses based on facial authentication are highly acceptable since the biological information can be acquired even if the users are not in contact with the apparatuses. The facial authentication and other noncontact-type personal authentication apparatuses are, however, poor in the accuracy of authentication as compared to the contact-type personal authentication apparatuses. Thus, the noncontact-type apparatuses are typically used as auxiliary means in combination with other authentication methods.

Related Art List
JPA laid open Publication No. Hei 6-155971

SUMMARY OF THE INVENTION

The present invention has been achieved in view of the foregoing background. It is thus a chief object of the present invention to provide a technology which improves the acceptability of a personal authentication apparatus.

To solve the foregoing problem, a biological information processing apparatus according to one of the aspects of the present invention acquires biological information, converts this biological information with a predetermined conversion function to generate personal data according to a user, and outputs it to exterior.

Another aspect of the present invention is a personal authentication apparatus. This apparatus acquires personal data, or biological information converted with a predetermined conversion function, from an external apparatus, and performs personal authentication by restoring the biological information from the personal data.

When the biological information processing apparatus is provided as a dedicated apparatus for each user, the user is prevented from having the psychological resistance against contact-type authentication apparatuses. Since the biological information processing apparatus itself need not contain personal information such as biological information, a security threat is less likely to occur even if the biological information processing apparatus is lost due to loss or theft. Moreover, since the biological information processing apparatus does not output the biological data but the personal data converted from biological data to the personal authentication apparatus, privacy protection is easier.

DETAILED DESCRIPTION OF THE INVENTION

The invention will now be described based on the preferred embodiments. This does not intend to limit the scope of the present invention, but exemplify the invention.

Figure 1:
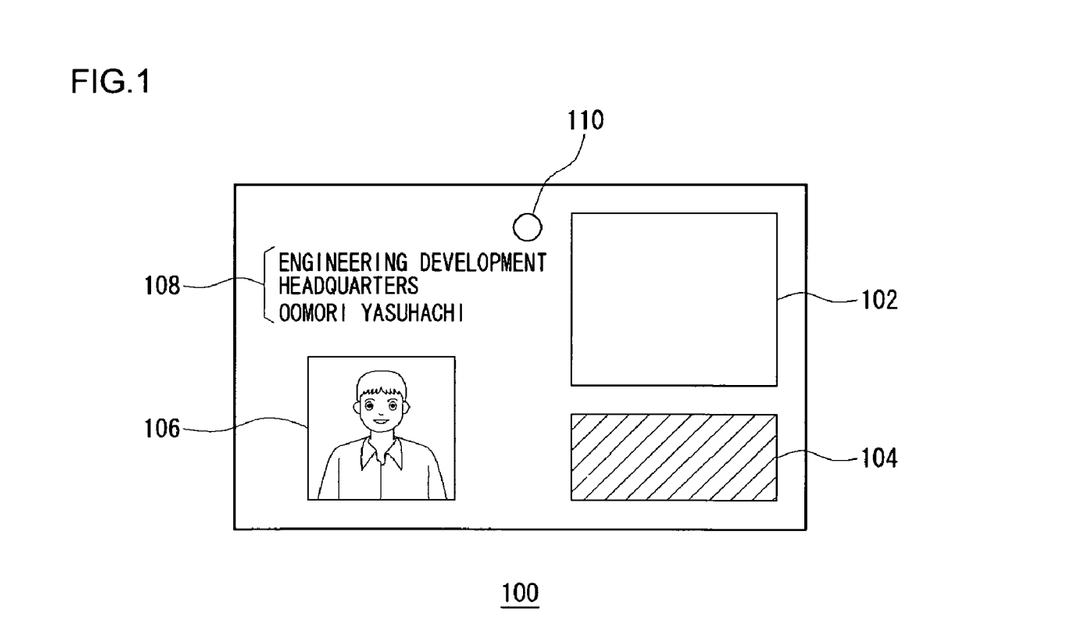
FIG. 1 is a diagram showing the appearance of a biological information processing apparatus.

FIG. 1 is a diagram showing the appearance of a biological information processing apparatus 100.

The user of the biological information processing apparatus 100 is a company employee. The biological information processing apparatus 100 is formed like a card as shown in the diagram. The biological information processing apparatus 100 is distributed to every employee for the sake of employee authentication in the company. A name display area 108 shows the post and name of the user. A photograph display area 106 is one to which a portrait of the user is attached. A piezoelectric device is arranged on the surface of a fingerprint sensor 104, and detects a fingerprint input from the user. The biological information processing apparatus 100 generates a two-dimensional code for authenticating the user based on shape information on fingerprints (hereinafter, referred to simply as "fingerprint information") detected by the fingerprint sensor 104. When the user puts one of his/her fingers on the fingerprint sensor 104 with the biological information processing apparatus 100 held toward a camera provided on an external personal authentication apparatus, a code display unit 102 displays the two-dimensional code generated. The two-dimensional code may be bar-code information such as QR (Quick Response) code (TM). A communication unit 110 transmits and receives various types of control signals to/from an external apparatus such as the personal authentication apparatus.

Figure 2:
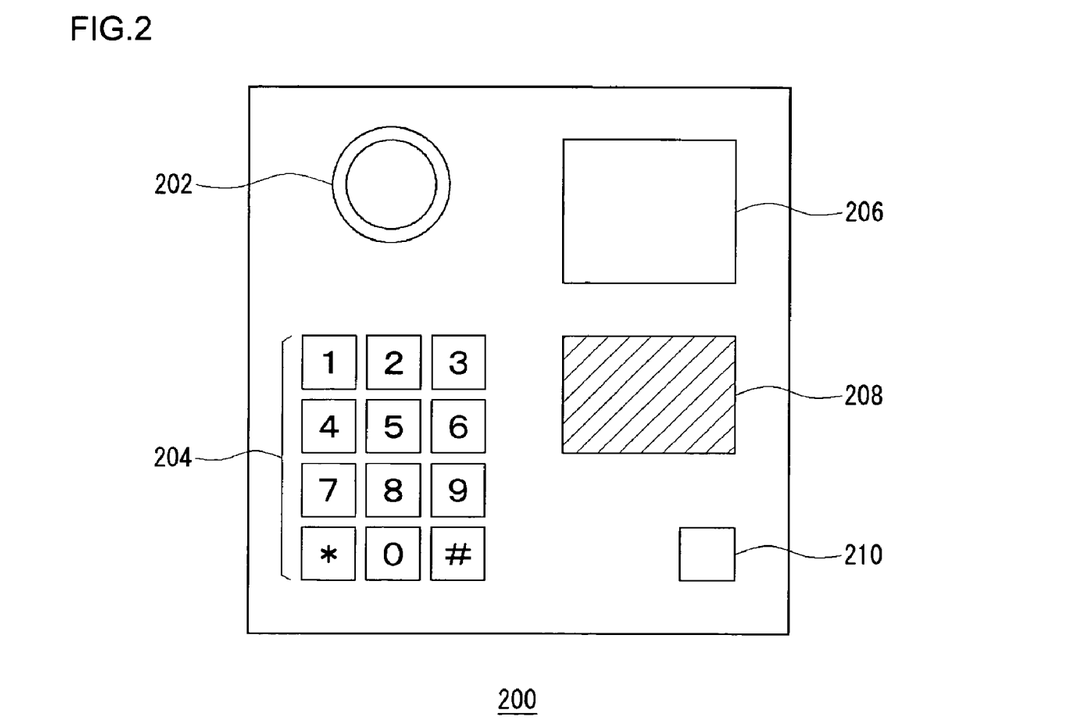
FIG. 2 is a diagram showing the appearance of a personal authentication apparatus.

FIG. 2 is a diagram showing the appearance of a personal authentication apparatus 200.

A camera 202 captures the image of the two-dimensional code displayed on the code display unit 102. The personal authentication apparatus 200 extracts the fingerprint information on the user from this two-dimensional code, and performs authentication processing. A key operation unit 204 accepts operation inputs from the user. A display unit 206 displays various types of information to the user. A piezoelectric device is arranged on the surface of a fingerprint sensor 208, and detects a fingerprint input from the user. The fingerprint sensor 208 can acquire fingerprint information with higher precision than the fingerprint sensor 104 of the biological information processing apparatus 100 does. Since fingerprint inputs are usually made from the fingerprint sensor 104 of the biological information processing apparatus 100, the number of times the fingerprint sensor 208 is used is relatively small. The fingerprint sensor 208 of the personal authentication apparatus 200 is used as auxiliary means for the fingerprint sensor 104 of the biological information processing apparatus 100.

For example, the fingerprints of aged persons are often worn out and are difficult to extract features from. Some users also have fingerprints difficult to extract features from due to illness or injury. In addition, some users may leave their biological information processing apparatuses 100 behind. In such cases, the fingerprint sensor 208 is used to acquire the fingerprint information of the users with higher precision. Moreover, when the personal authentication apparatus 200 determines that user authentication cannot be concluded from the fingerprint information acquired by the biological information processing apparatus 100, the personal authentication apparatus 200 may instruct the user to perform fingerprint authentication by using the fingerprint sensor 208. A communication unit 210 transmits and receives various types of control signals to/from an external apparatus such as the biological information processing apparatus 100.

Incidentally, the personal authentication apparatus 200 may acquire biological information other than fingerprints to perform combined authentication. For example, the personal authentication apparatus 200 may acquire facial or iris-based biological data through the camera 202. The personal authentication apparatus 200 may perform authentication processing by using such biological information and the fingerprint information in combination. The personal authentication apparatus 200 may also perform password-based authentication at the same time, based on operation inputs of the user through the key operation unit 204.

Hereinafter, description will be given of two embodiments, or a first embodiment and a second embodiment, of the present invention.

The first and second embodiments shall be identical in respects pertaining to FIGS. 1 and 2.

First Embodiment

Figure 3:
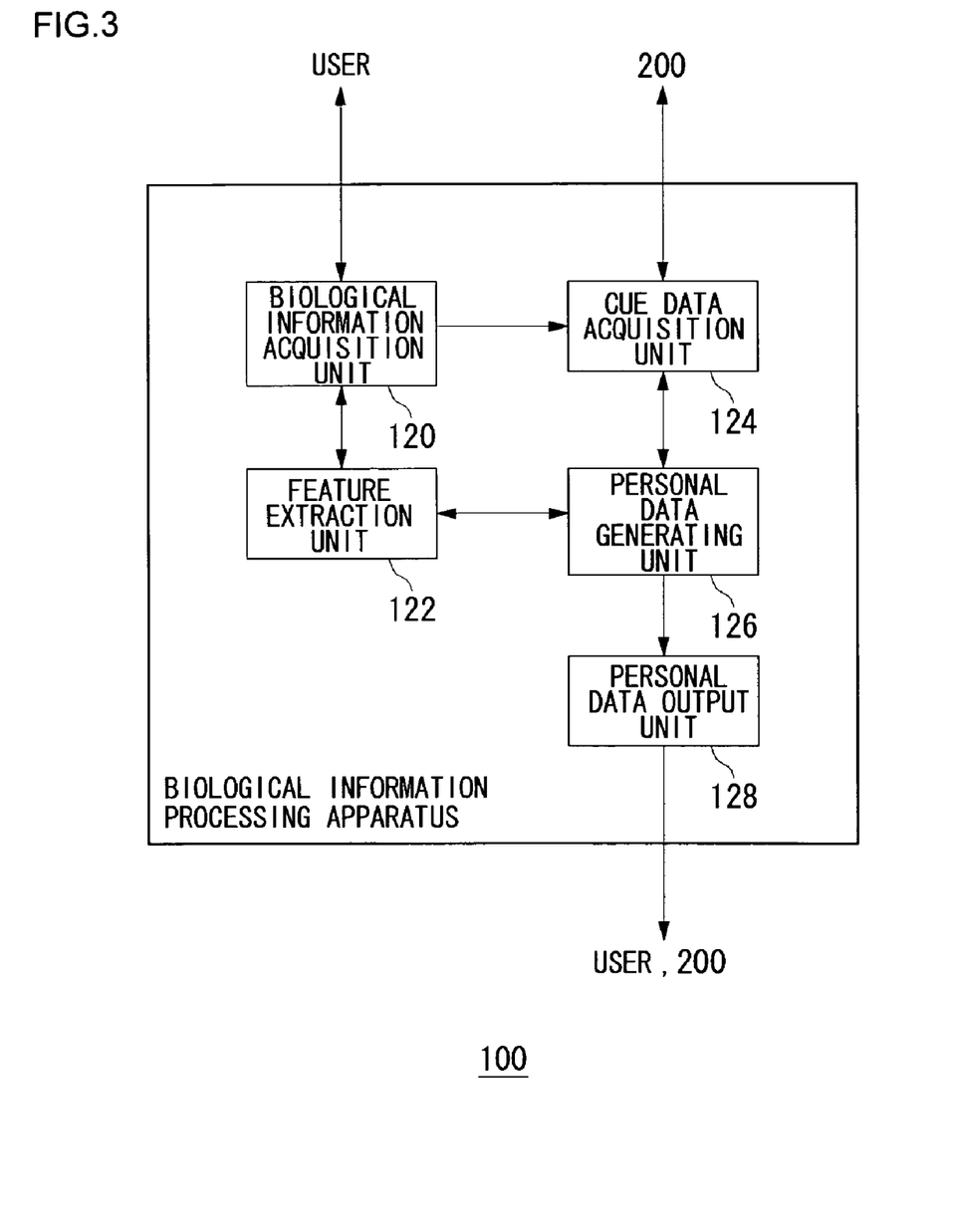
FIG. 3 is a functional block diagram of the biological information processing apparatus according to a first embodiment.

FIG. 3 is a functional block diagram of the biological information processing apparatus 100 according to the first embodiment.

In terms of hardware, the individual blocks shown here can be achieved by devices and mechanical apparatuses, including a computer CPU. In terms of software, they can be achieved by a computer program and the like. Here, the shown functional blocks shall be achieved by cooperation thereof. It will therefore be understood by those skilled in the art that these functional blocks can be realized in various forms depending on the combination of hardware and software.

The biological information processing apparatus 100 includes a biological information acquisition unit 120, a feature extraction unit 122, a cue data acquisition unit 124, a personal data generating unit 126, and a personal data output unit 128. The biological information acquisition unit 120 acquires the fingerprint information on the user as the biological information through the fingerprint sensor 104. The feature extraction unit 122 extracts features for personal authentication from the fingerprint information acquired by the biological information acquisition unit 120. For example, in the case of a fingerprint, the positions of branch points and end points in the fingerprint are extracted as the information for identifying the person. Hereinafter, the information on the features that the feature extraction unit 122 extracts from the biological information, such as a fingerprint, acquired by the biological information acquisition unit 120 will be referred to as "biological feature information" when emphasized.

The cue data acquisition unit 124 transmits and receives cue data to/from the personal authentication apparatus 200 through the communication unit 110. The cue data refers to key data for hiding the biological data from exterior while the biological information processing apparatus 100 and the personal authentication apparatus 200 handle the biological information. This cue data plays the role of a one-time password with which the biological information processing apparatus 100 sends the biological information to the personal authentication apparatus 200. When the biological information acquisition unit 120 acquires the biological information from the user, the cue data acquisition unit 124 requests cue data from the personal authentication apparatus 200. In response to this request, the personal authentication apparatus 200 transmits the cue data. The cue data acquisition unit 124 acquires this cue data through the communication unit 110. The personal data generating unit 126 encrypts personal data which is converted from the biological feature information with a predetermined function, based on the cue data acquired by the cue data acquisition unit 124. The personal data is data for identifying the user, including the biological information. The personal data generating unit 126 generates the personal data in the form of a two-dimensional code. The personal data output unit 128 includes the code display unit 102, and outputs the encrypted personal data through the data display unit 102. In the present embodiment, the personal data output unit 128 outputs the personal data to exterior by means of image display via the code display unit 102.

Figure 4:
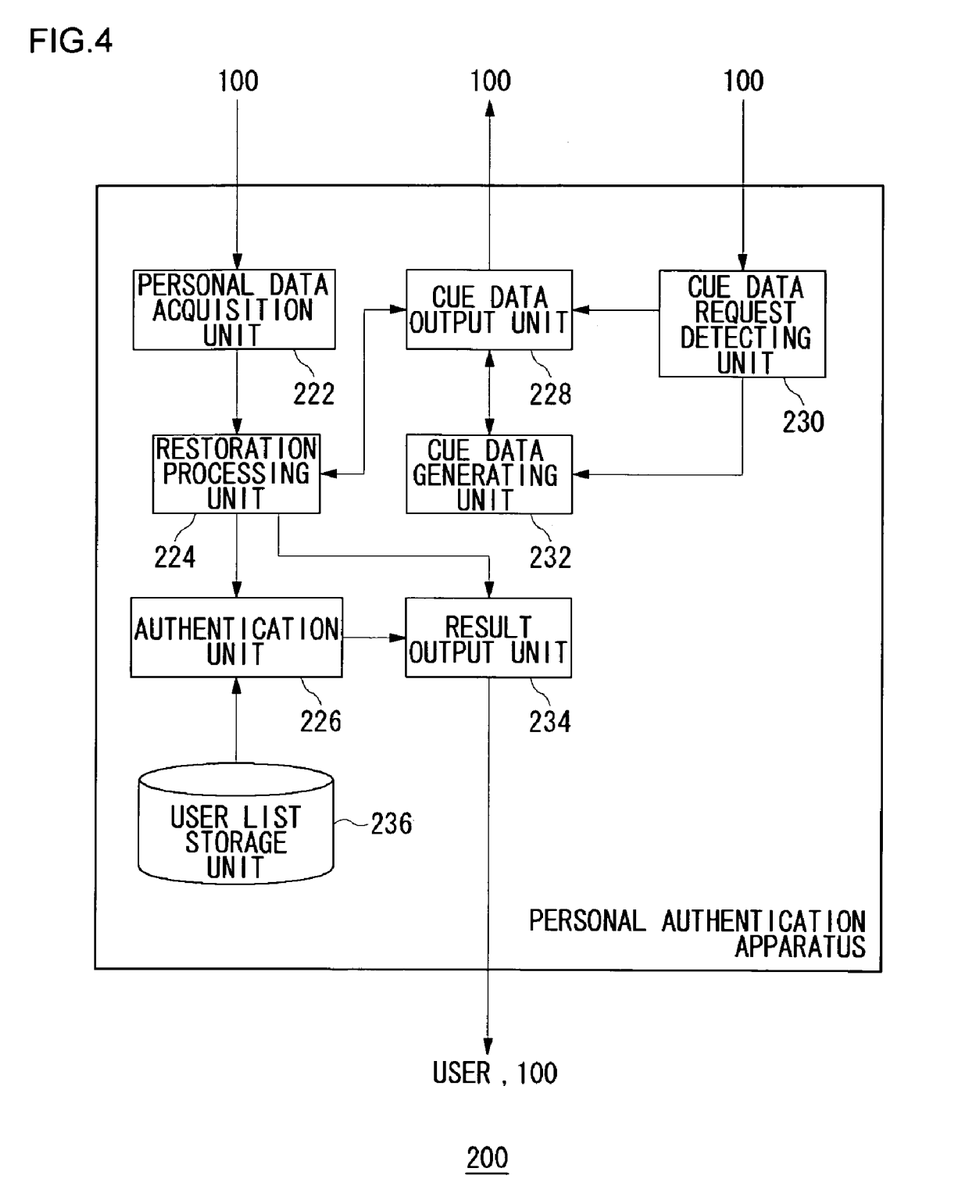
FIG. 4 is a functional block diagram of the personal authentication apparatus according to the first embodiment.

FIG. 4 is a functional block diagram of the image processing apparatus 200 according to the first embodiment.

In terms of hardware, the individual blocks shown here can be achieved by devices and mechanical apparatuses, including a computer CPU. In terms of software, they can be achieved by a computer program and the like. Here, the shown functional blocks are achieved by cooperation thereof. It will therefore be understood by those skilled in the art that these functional blocks can be realized in various forms depending on the combination of hardware and software.

The personal authentication apparatus 200 includes a personal data acquisition unit 222, a restoration processing unit 224, an authentication unit 226, a cue data output unit 228, a cue data request detecting unit 230, a cue data generating unit 232, a result output unit 234, and a user list storage unit 236. The cue data request detecting unit 230 receives the request for cue data from the cue data acquisition unit 124 through the communication unit 210. When the cue data request detecting unit 230 detects the request for cue data, it instructs the cue data generating unit 232 to generate the cue data. The cue data generating unit 232 generates time information as the cue data. The cue data generating unit 232 may generate the cue data from external environmental data such as air temperature, or from random numbers etc. The cue data is generated as text or binary data of several bytes or so. The cue data output unit 228 transmits the cue data generated by the cue data generating circuit 232 to the biological information processing apparatus 100 through the communication unit 210. The cue data output unit 228 stores the transmitted cue data for a predetermined time.

The personal data acquisition unit 222 receives the personal data from the biological information processing apparatus 100. This personal data is encrypted by the cue data transmitted by the cue data output unit 228. The restoration processing unit 224 decrypts this encrypted personal data by using the cue data stored in the cue data output unit 228. Incidentally, if the predetermined time has elapsed and the cue data is no longer stored in the cue data output unit 228, the result output unit 234 notifies the user of failed authentication. The restoration processing unit 224 converts this decrypted personal data with a predetermined conversion function, thereby extracting the biological feature information. The user list storage unit 236 contains a registered user list in which valid users to be authenticated and their biological feature information are associated with each other. The authentication unit 226 performs authentication processing by searching the registered user list for biological feature information having high similarity to the biological feature information extracted by the restoration processing unit 224. The result output unit 234 notifies the user of the result of authentication through the display unit 206. The result of authentication may be transmitted to an external apparatus via the communication unit 210. The user list storage unit 236 may be arranged outside the personal authentication apparatus 200.

The personal authentication apparatus 200 may further comprises an operation input unit which accepts operation inputs of the user from the key operation unit 204 and processing the same, and a biological information acquisition unit which acquires fingerprint, facial, and other biological information through the camera 202 or the fingerprint sensor 208.

Figure 5:
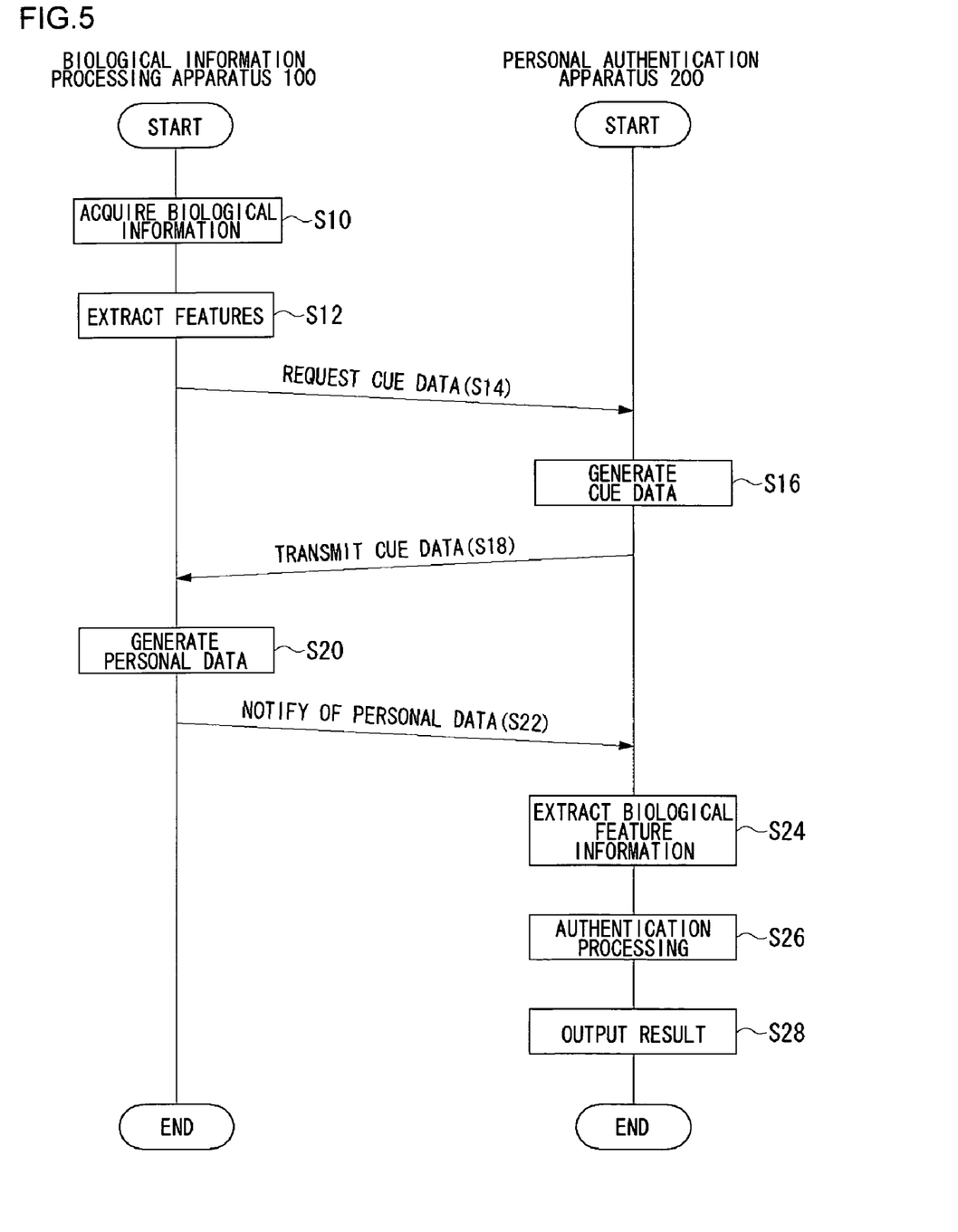
FIG. 5 is a sequence diagram showing the process of the biological authentication according to the first embodiment.

FIG. 5 is a sequence diagram showing the process of the biological authentication according to the first embodiment.

The user puts one of his/her fingers on the fingerprint sensor 104 with the biological information processing apparatus 100 held toward the personal authentication apparatus 200. The biological information acquisition unit 120 acquires the fingerprint information as the biological information through the fingerprint sensor 104 (S10). The feature extraction unit 122 extracts the features of the fingerprint acquired as the biological information (S12). The cue data acquisition unit 124 requests cue data from the personal authentication apparatus 200 (S14). The cue data request detecting unit 230 detects the request for cue data. The cue data generating unit 232 generates the cue data under an instruction from the cue data request detecting unit 230 (S16). The cue data output unit 228 transmits the cue data to the biological information processing apparatus 100 (S18).

The cue data acquisition unit 124 receives the cue data. The personal data generating unit 126 encrypts the biological feature information acquired at S12 based on the cue data received at S18. The personal data generating unit 126 applies conversion processing to the encrypted biological feature information to generate the personal data in the form of a two-dimensional code (S20). The personal data output unit 128 notifies the personal authentication apparatus 200 of the personal data (S22). The personal authentication apparatus 200 captures the image of this two-dimensional code through the camera 202. The personal data acquisition unit 222 thus acquires the personal data. The restoration processing unit 224 decrypts the personal data based on the cue data transmitted at S18, and then extracts the biological feature information (S24). The authentication unit 226 performs authentication processing based on the biological feature information extracted (S26). The result output unit 234 displays the result of authentication on the display unit 206 (S28).

Aside from the two-dimensional code, the biological information processing apparatus 100 may generate the personal data as a digital or analog signal in a predetermined format. The biological information processing apparatus 100 may transmit the personal data to the personal authentication apparatus 200 by air over a predetermined frequency band. Otherwise, the biological information processing apparatus 100 may transmit the personal data to the personal authentication apparatus 200 by using various media capable of information transmission, such as sound waves and magnetism. The biological information processing apparatus 100 may transmit the biological information to the personal authentication apparatus 200 without converting it into personal data. This might lower the level of security as compared to the case with the biological information processing apparatus 100 shown in the present embodiment. It is possible, however, to design the biological information processing apparatus 100 and the personal authentication apparatus 200 more simply. The biological information processing apparatus 100 may have the same function as that of the cue data generating unit 232 of the personal authentication apparatus 200. In this case, it is possible to omit the negotiation for the cue data, and omit the cue data acquisition unit 124, the cue data request detecting unit 230, and the cue data output unit 228 necessary for the negotiation. In the present embodiment, the code generated as the image data to be displayed on the code display unit 102 is captured by the camera 202, so that the personal data generated by the biological information processing apparatus 100 is transmitted to the personal authentication apparatus 200. According to this method, the biological information processing apparatus 100 requires no electric power for transmitting the personal data. This also eliminates the possibility of interception unlike with wireless means, whereby the security is even enhanced.

Figure 6:
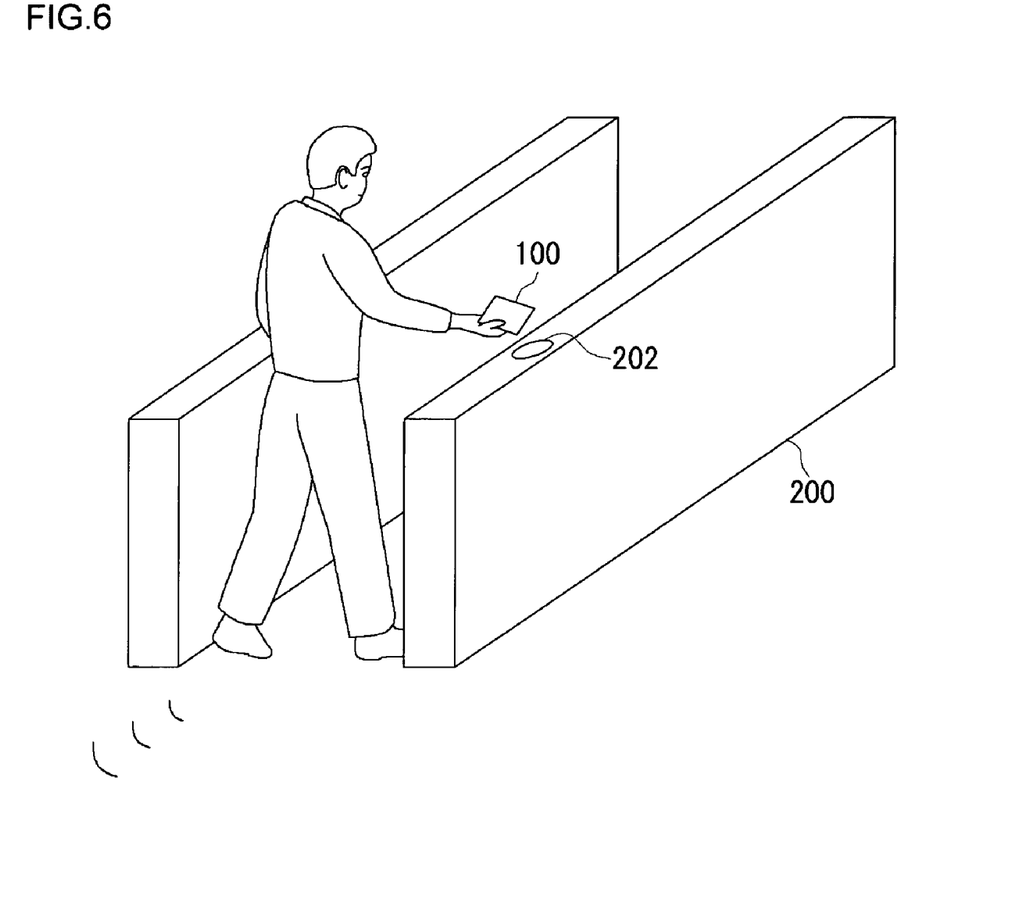
FIG. 6 is a diagram showing another configuration of the personal authentication apparatus according to the first embodiment.

FIG. 6 is a diagram showing another hardware configuration of the personal authentication apparatus 200 according to the first embodiment.

As shown in the diagram, the personal authentication apparatus 200 may be formed so that users can pass through. The camera 202 is arranged in the top of the personal authentication apparatus 200. The user sends his/her personal data to the personal authentication apparatus 200 with the biological information processing apparatus 100 held toward the camera 202.

The configuration shown in the diagram is useful, for example, for checking passengers who are getting on board a plane. The personal authentication apparatus 200 contains a record of, for example, the biological information on international criminals such as past hijackers. When the biological information acquired from a user matches with the biological information on these criminals, the personal authentication apparatus 200 may operate to interrupt the passage of the user.

Up to this point, the first embodiment has been described.

Now, description will be given of a second embodiment, which will deal with an aspect in which the authentication processing is performed on condition that the biological information processing apparatus 100 lies within a predetermined range as viewed from the personal authentication apparatus 200.

Second Embodiment

Figure 7:
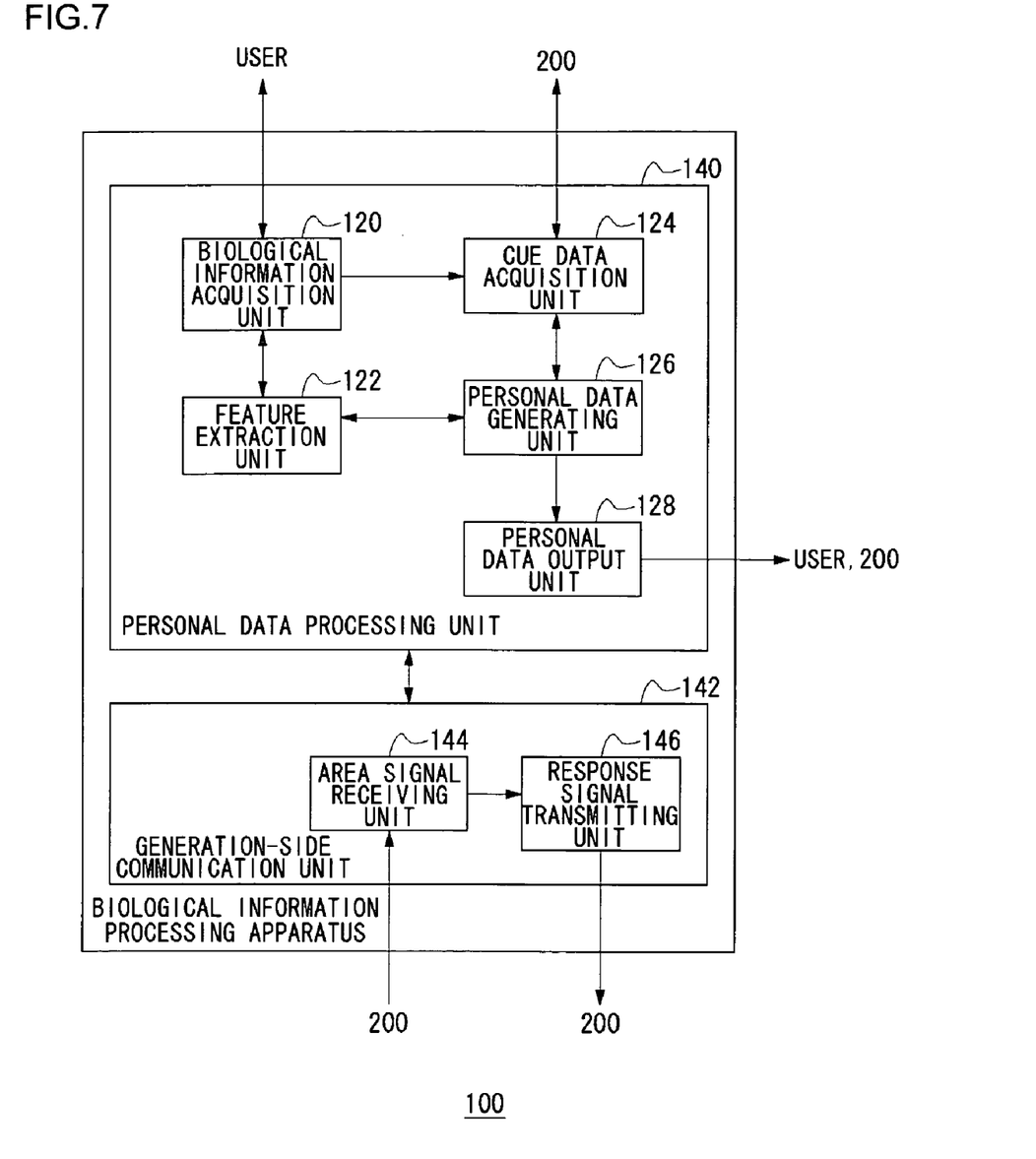
FIG. 7 is a functional block diagram of the biological information processing apparatus according to a second embodiment.

FIG. 7 is a functional block diagram of the biological information processing apparatus according to the second embodiment.

In the second embodiment, the biological information processing apparatus 100 includes a personal data processing unit 140 and a generation-side communication unit 142.

The personal data processing unit 140 includes a biological information acquisition unit 120, a feature extraction unit 122, a cue data acquisition unit 124, a personal data generating unit 126, and a personal data output unit 128.

Here, the functional blocks included in the personal data processing unit 140 have the same functions as those of the respective functional blocks of the biological information processing apparatus 100 described in the first embodiment with reference to FIG. 3, being designated by identical reference numerals.

The biological information processing apparatus 100 of the second embodiment differs from the biological information processing apparatus 100 of the first embodiment in that the generation-side communication unit 142 is added thereto.

The generation-side communication unit 142 is a block for controlling communication with the personal authentication apparatus 200, and includes an area signal receiving unit 144 and a response signal transmitting unit 146.

The area signal receiving unit 144 detects an area signal transmitted from the personal authentication apparatus 200.

The personal authentication apparatus 200 according to the second embodiment transmits a signal for detecting whether or not the biological information processing apparatus 100 lies inside a predetermined range, or the area signal, to within the range.

When the area signal receiving unit 144 receives the area signal, the response signal transmitting unit 146 transmits a response signal to the personal authentication apparatus 200.

The response signal is a signal by which the biological information processing apparatus 100 notifies the personal authentication apparatus 200 of the reception of the area signal.

The response signal may include data for identifying the biological information processing apparatus 100. The personal authentication apparatus 200, or the sender of the area signal, receives the response signal from the biological information processing apparatus 100, and thus recognizes that the biological information processing apparatus 100 lies within the range of transmission of the area signal.

The generation-side communication unit 142 may transmit and receive data to/from the personal authentication apparatus 200 through the communication unit 110.

The biological information processing apparatus 100 is driven by electricity that is fed by radio waves for carrying the area signal.

The mechanism may be achieved through the application of known feeding methods that are used for so-called passive type RFID (Radio Frequency Identification) tags.

For example, the possible methods for feeding electricity from the personal authentication apparatus 200 to the biological information processing apparatus 100 include the following: an electrostatic coupling method which uses electrostatic induction; an electromagnetic coupling method which uses mutual induction of coils in an alternating field; an electromagnetic coupling method which uses voltages induced by fluxes of magnetic induction from two coils; and a microwave method which uses power supplied in the form of microwaves.

According to such an aspect, the biological information processing apparatus 100 will not be driven unless it detects the area signal. The personal data output unit 128 thus outputs personal data on condition that the area signal is received by the area signal receiving unit 144.

Figure 8:
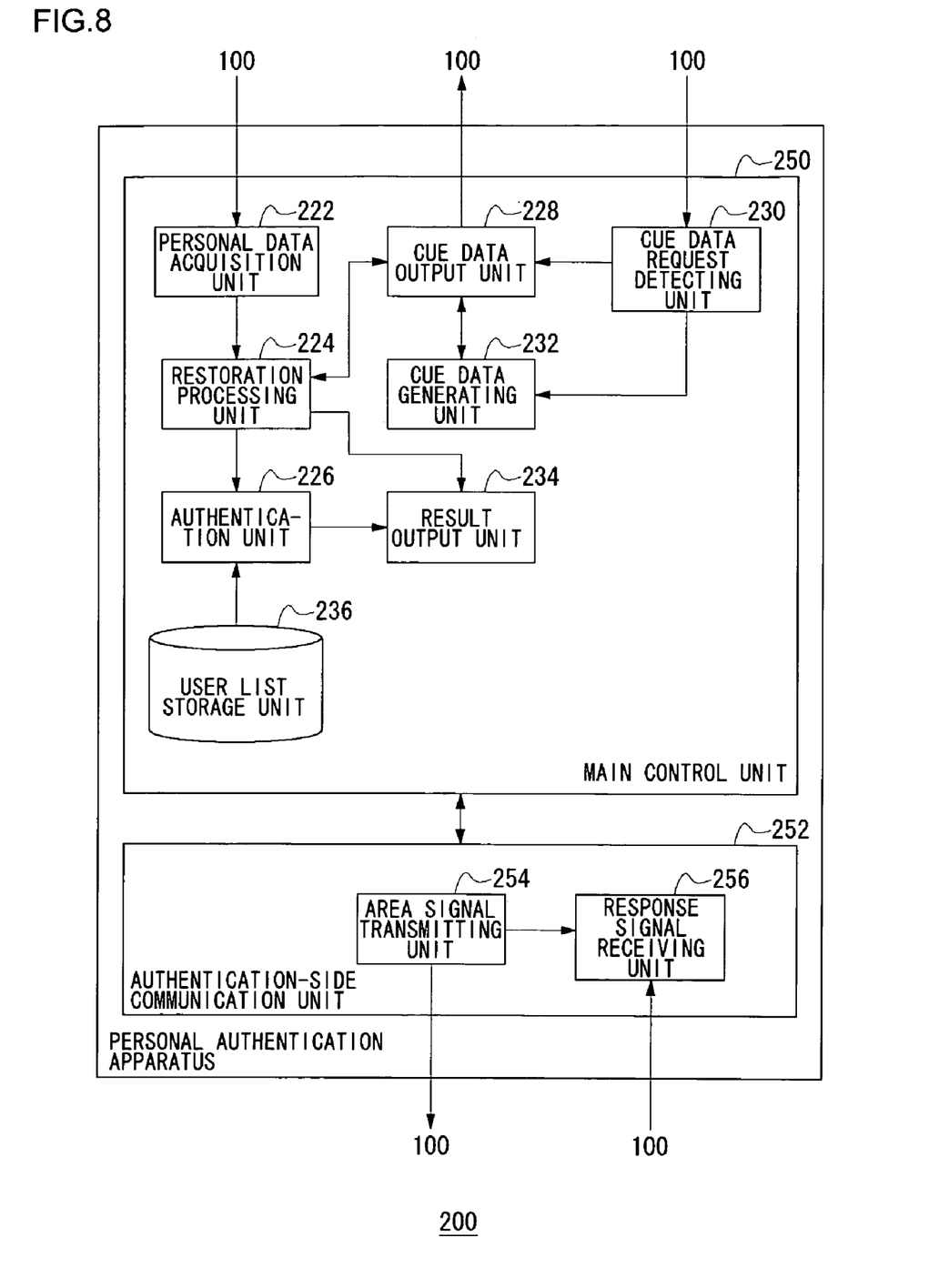
FIG. 8 is a functional block diagram of the personal authentication apparatus according to the second embodiment.

FIG. 8 is a functional block diagram of the personal authentication apparatus according to the second embodiment.

In the second embodiment, the personal authentication apparatus 200 includes a main control unit 250 and an authentication-side communication unit 252.

Here, the main control unit 250 includes a personal data acquisition unit 222, a restoration processing unit 224, an authentication unit 226, a cue data output unit 228, a cue data request detecting unit 230, a cue data generating unit 232, a result output unit 234, and a user list storage unit 236.

The functional blocks included in the main control unit 250 have the same functions as those of the respective functional blocks of the personal authentication apparatus 200 described in the first embodiment with reference to FIG. 4, being designated by identical reference numerals.

The personal authentication apparatus 200 of the second embodiment differs from the personal authentication apparatus 200 of the first embodiment in that the authentication-side communication unit 252 is added thereto.

The authentication-side communication unit 252 is a block for controlling communication with the biological information processing apparatus 100, and includes an area signal transmitting unit 254 and a response signal receiving unit 256.

The area signal transmitting unit 254 transmits the area signal in order to detect whether or not the biological information processing apparatus 100 lies within a predetermined range.

This area signal may be transmitted to a circular area around the personal authentication apparatus 200 with a radius of predetermined distance, or may be transmitted to an area that is directional in a certain direction as viewed from the personal authentication apparatus 200.

The area signal is transmitted to distances between 10 cm and 2 m or so from the personal authentication apparatus 200 in the form of radio waves.

The response signal receiving unit 256 receives the response signal transmitted from the biological information processing apparatus 100.

When the response signal receiving unit 256 receives the response signal, the personal authentication apparatus 200 recognizes that a biological information processing apparatus 100 lies within the range of transmission of the area signal.

When the response signal includes information for identifying the biological information processing apparatus 100, the personal authentication apparatus 200 can identify which biological information processing apparatus 100 lies in the range of transmission of the area signal.

The response signal receiving unit 256 also determines the distance from the personal authentication apparatus 200 to the biological information processing apparatus 100 based on the intensity of reception of the response signal.

For example, the response signal receiving unit 256 may determine the distance to the biological information processing apparatus 100 based on the intensity of reception of the response signal, by consulting a data table in which intensities of reception of the response signal and distances to the biological information processing apparatus 100 are associated in advance.

The authentication-side communication unit 252 may transmit and receive data to/from the biological information processing apparatus 100 through the communication unit 210.

The personal data acquisition unit 222 acquires personal data by capturing two-dimensional code which is displayed on the code display unit 102 of the biological information processing apparatus 100.

Here, the personal data acquisition unit 222 adjusts the focal length for capturing the two-dimensional code in accordance with the distance to the biological information processing device 100 which is determined by the response signal receiving unit 256.

According to such an aspect, the personal authentication apparatus 200 can acquire the two-dimensional code, or the personal data, more favorably.

Figure 9:
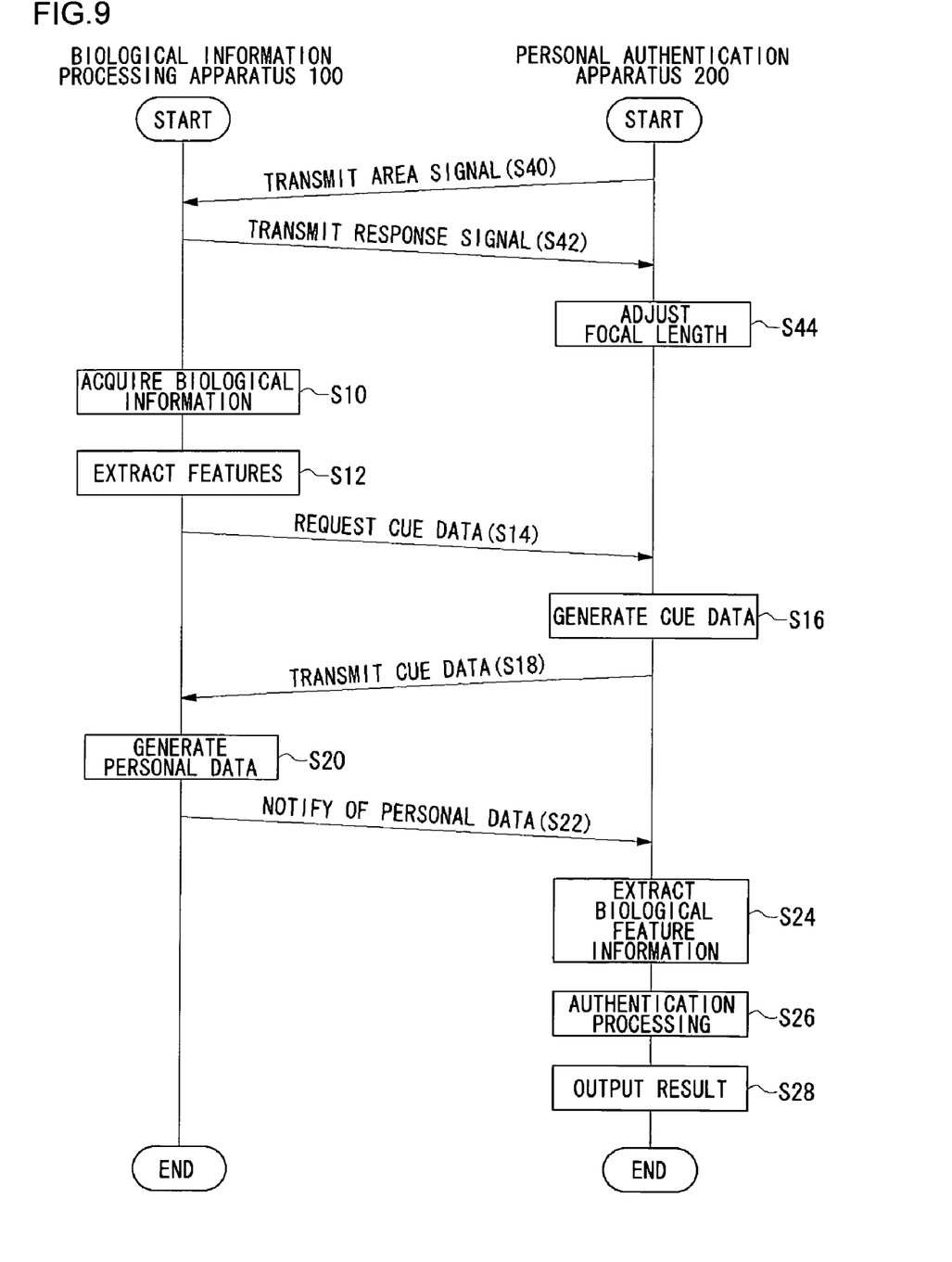
FIG. 9 is a sequence diagram showing the process of the biological authentication according to the second embodiment.

FIG. 9 is a sequence diagram showing the process of the biological authentication according to the second embodiment.

The area signal transmitting unit 254 of the personal authentication apparatus 200 transmits the area signal at regular time intervals (S40).

When the area signal receiving unit 144 of the biological information processing apparatus 100 receives the area signal, the response signal transmitting unit 146 transmits the response signal to the personal authentication apparatus 200 (S42).

When the area signal receiving unit 144 receives the area signal, the biological information processing apparatus 100 is fed with electricity by the radio waves that carry the area signal.

This feeding allows the functional blocks included in the main control unit 250 of the biological information processing apparatus 100 to perform their respective processes.

The response signal receiving unit 256 of the personal authentication apparatus 200 determines the distance between the personal authentication apparatus 200 and the biological information processing apparatus 100 based on the intensity of the response signal received.

According to this distance determined, the personal data acquisition unit 222 adjusts the focal length of the camera 202 (S44).

Here, the personal data acquisition unit 222 may also adjust such shooting conditions as the shutter speed of the camera 202 in accordance with other shooting circumstances such as outside light.

Up to this point, the second embodiment has been described.

As above, according to the present embodiment, the biological information processing apparatus 100 itself need not contain personal information. That is, since biological information processing apparatuses 100 need not be individualized one by one, they are fit for mass production. Moreover, since the biological information processing apparatus 100 contains no personal information, there is the merit of no security threat even in case the user loses his/her biological information processing apparatus 100. The personal authentication system of the present embodiment, consisting of the biological information processing apparatus 100 and the personal authentication apparatus 200, allows both the merit of high accuracy authentication of a contact-type personal authentication apparatus and the merit of high acceptability of a non-contact type personal authentication apparatus.

Moreover, in the second embodiment, the personal authentication processing will not be performed unless the biological information processing apparatus 100 lies within the range of transmission of the area signal from the personal authentication apparatus 200. This allows enhanced security for the data transmission and reception between the biological information processing apparatus 100 and the personal authentication apparatus 200.

The biological information processing apparatus 100 according to the second embodiment obtains the power necessary for its operation from exterior. Thus, the biological information processing apparatus 100 itself need not have any power source.

This not only improves the convenience of use of the biological information processing apparatus 100, but also suppresses the manufacturing cost of the biological information processing apparatus 100 effectively.

The range of transmission of the area signal may be set to near the front of the camera 202 of the personal authentication apparatus 200. This makes it easier for the personal authentication apparatus 200 to capture the two-dimensional code displayed on the biological information processing apparatus 100. When the data to be transmitted as the area signal and the response signal is encrypted for transmission and reception, the biological information processing apparatus 100 and the personal authentication apparatus 200 can be easily prevented from performing processing due to unauthorized signals. This can enhance the security further.

After the reception of the response signal, the personal authentication apparatus 200 may stop transmitting the area signal until the authentication processing by the authentication unit 226 completes. According to such an aspect, it is possible to suppress the power consumption ascribable to the transmission of the area signal from the personal authentication apparatus 200.

Up to this point, the present invention has been described in conjunction with the embodiment. It should be noted that the present invention is not limited to this embodiment, and various modifications thereof are also applicable as aspects of the present invention.

The biological information processing apparatus 100 may have the code display unit 102 on its top surface and the fingerprint sensor 104 on its bottom surface. The whole area of the top surface or bottom surface may be configured as the fingerprint sensor 104. The biological information processing apparatus 100 may be realized in the form of a cellular phone or a personal digital assistant (PDA). The user may make a fingerprint input from a fingerprint sensor 104 formed on these mobile apparatuses. While the biological information processing apparatus 100 of the present embodiment acquires the fingerprint information as the biological information, the present invention may also be applied with various known types of biological information such as irises, skin thicknesses, and vein patterns.

What is claimed is:

1. A biological information processing apparatus comprising:
   a biological information acquisition unit which acquires biological information;
   a personal data generating unit which coverts the biological information with a predetermined conversion function into an image so as to generate personal data according to a user in the form of image data;
   a personal data output unit which outputs the image to a display unit for being captured by a capturing unit of a personal authentication apparatus, wherein the personal authentication apparatus restores the biological information from the image captured by the capturing unit and performs personal authentication by searching a registered user list for the biological information restored, biological information on users being registered on the registered user list in advance, and
   a cue data acquisition unit which acquires, from the personal authentication apparatus, predetermined cue data used as a key to be shared by the personal authentication apparatus and the biological information processing apparatus, and wherein
   the personal data generating unit encrypts the personal data based on the cue data.

2. The biological information processing apparatus according to claim 1, further comprising
   an area signal receiving unit which receives a predetermined area signal from the personal authentication apparatus, the area signal being transmitted to within a predetermined range as viewed from the personal authentication apparatus, and wherein
   the personal data output unit outputs the personal data to the personal authentication apparatus on condition that the area signal is received.

3. The biological information processing apparatus according to claim 2, wherein the personal data output unit outputs the personal data to the personal authentication apparatus by using power supplied by radio waves for carrying the area signal.

4. The biological information processing apparatus according to claim 1, wherein the personal data output unit outputs the personal data to the personal authentication apparatus by using power supplied from an external apparatus.

5. A personal authentication apparatus comprising:
   a cue data output unit which outputs predetermined cue data, used as a key to be shared by a biological information processing apparatus and the personal authentication apparatus, to the biological information processing apparatus;
   a personal data acquisition unit which acquires an image displayed on the biological information processing apparatus by a capturing unit, wherein the image represents biological information which is encrypted by the cue data and is converted with a predetermined conversion function;
   a restoration processing unit which restores the biological information from the image acquired by the capturing unit based on the cue data; and
   an authentication unit which performs personal authentication by searching a registered user list for the biological information restored, biological information on users being registered on the registered user list in advance.

6. The personal authentication apparatus according to claim 5, further comprising:
   an area signal transmitting unit which transmits a predetermined area signal for detecting whether or not the biological information processing apparatus lies within a predetermined range from the personal authentication apparatus; and
   a response signal receiving unit which receives a response signal responding to the area signal, from the biological information processing apparatus receiving the area signal, and wherein
   the authentication unit performs personal authentication on condition that the response signal is received.

7. The personal authentication apparatus according to claim 6, wherein
   when the personal data generated as image data is displayed as an image on the biological information processing apparatus, the personal data acquisition unit acquires the personal data from the biological information processing apparatus by shooting the image at a focal length corresponding to intensity of the response signal responding to the area signal.

8. A system comprising a biological information processing apparatus which acquires biological information and a personal authentication apparatus which performs personal authentication based on the biological information, wherein:
   the biological information processing apparatus includes
      a personal data generating unit which converts the biological information with a predetermined conversion function into an image so as to generate personal data according to a user in the form of image data, and
      a personal data output unit which outputs the image to a display unit; and
   the personal authentication apparatus includes
      a cue data output unit which outputs predetermined cue data, used as a key to be shared by the biological information processing apparatus and the personal authentication apparatus, to the biological information processing apparatus;
      a personal data acquisition unit which acquires an image displayed on the display unit of the biological information processing apparatus by a capturing unit, wherein the image represents biological information which is encrypted by the cue data and is converted with the predetermined conversion function,
      a restoration processing unit which restores the biological information from the image acquired by the capturing unit based on the cue data, and
      an authentication unit which performs personal authentication by searching a registered user list for the biological information restored, biological information on users being registered on the registered user list in advance.

9. A biological information processing apparatus comprising:
   a biological information acquisition unit which acquires biological information;
   a personal data generating unit which converts the biological information with a predetermined conversion function into an image so as to generate personal data according to a user in the form of image data;

a personal data output unit which outputs the image to a display unit for being captured by a capturing unit of a personal authentication apparatus, wherein the personal authentication apparatus restores the biological information from the image captured by the capturing unit;

a cue data acquisition unit which acquires, from the personal authentication apparatus, predetermined cue data used as a key to be shared by the personal authentication apparatus and the biological information processing apparatus, wherein the personal data generating unit encrypts the personal data based on the cue data; and an area signal receiving unit which receives a predetermined area signal from the personal authentication apparatus, the area signal being transmitted to within a predetermined range as viewed from the personal authentication apparatus, wherein the personal data output unit outputs the personal data to the personal authentication apparatus on condition that the area signal is received.

10. The biological information processing apparatus according to claim 9, wherein the personal data output unit outputs the personal data to the personal authentication apparatus by using power supplied by radio waves for carrying the area signal.

* * * * *